(12) United States Patent
Gollier

(10) Patent No.: US 7,239,395 B2
(45) Date of Patent: Jul. 3, 2007

(54) OPTICAL INTERROGATION SYSTEMS WITH REDUCED PARASITIC REFLECTIONS AND A METHOD FOR FILTERING PARASITIC REFLECTIONS

(75) Inventor: Jacques Gollier, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 336 days.

(21) Appl. No.: 10/856,572

(22) Filed: May 27, 2004

(65) Prior Publication Data

US 2005/0264818 A1    Dec. 1, 2005

(51) Int. Cl.
*G01N 21/55* (2006.01)
*G01J 4/00* (2006.01)

(52) U.S. Cl. ..................... 356/445; 356/369
(58) Field of Classification Search ............ None
See application file for complete search history.

(56) References Cited

U.S. PATENT DOCUMENTS

| | | | | |
|---|---|---|---|---|
| 5,408,354 | A | 4/1995 | Hosokawa | 356/73 |
| 6,014,204 | A | 1/2000 | Prahl et al. | 359/281 |
| 6,218,194 | B1 | 4/2001 | Lyndin et al. | 436/518 |
| 2002/0127565 | A1 | 9/2002 | Cunningham et al. | 435/6 |
| 2002/0168295 | A1 | 11/2002 | Cunningham et al. | 422/82.05 |
| 2003/0017580 | A1 | 1/2003 | Cunningham et al. | 435/287.2 |
| 2003/0017581 | A1 | 1/2003 | Li et al. | 435/287.2 |
| 2003/0026891 | A1 | 2/2003 | Qiu et al. | 427/58 |
| 2003/0027327 | A1 | 2/2003 | Cunningham et al. | 435/287.2 |
| 2003/0027328 | A1 | 2/2003 | Cunningham et al. | 435/287.2 |
| 2003/0032039 | A1 | 2/2003 | Cunningham et al. | 435/6 |
| 2003/0059855 | A1 | 3/2003 | Cunningham et al. | 435/7.9 |
| 2003/0068657 | A1 | 4/2003 | Lin et al. | 435/7.9 |
| 2003/0077660 | A1 | 4/2003 | Pien et al. | 435/7.1 |
| 2003/0092075 | A1 | 5/2003 | Pepper | 435/7.9 |
| 2003/0113766 | A1 | 6/2003 | Pepper et al. | 435/6 |
| 2004/0132172 | A1 | 7/2004 | Cunningham et al. | 435/287.2 |
| 2004/0132214 | A1 | 7/2004 | Lin et al. | 436/518 |
| 2004/0151626 | A1 | 8/2004 | Cunningham et al. | 422/58 |
| 2004/0223881 | A1 | 11/2004 | Cunningham et al. | 422/82.05 |
| 2005/0018944 | A1* | 1/2005 | Mozdy | 385/12 |

FOREIGN PATENT DOCUMENTS

DK    DE 4013125 A1 *    4/1990

OTHER PUBLICATIONS

Choquette, et al.; "Thermal detection of enzyme-labelled antigen-antibody complexes using fiber-optic interferometry"; Sensors and Actuators B 22 (1984) 89-96.

(Continued)

*Primary Examiner*—Michael P. Stafira
(74) *Attorney, Agent, or Firm*—Svetlana Z. Short

(57) ABSTRACT

According to one aspect of the present invention the optical interrogation system comprises: (i) an optical sensor capable of immobilizing biological, bio-chemical and/or chemical substance; and (ii) an optical isolator that filters and eliminates parasitic reflections introduced by the optical sensor. In some embodiments the optical sensor includes a GCW with a surface having a sensing region capable of immobilizing biological, bio-chemical or chemical substances includes, and the optical interrogation system includes an optical detection system for monitoring this sensing region, the optical detection system comprising a light source, an optical delivery system, and a detection instrument.

13 Claims, 7 Drawing Sheets

OTHER PUBLICATIONS

Brandenburg, et al.; "Direct observation of affinity reactions by reflected-mode operation of integrated optical grating coupler"; Sensors and Actuators B 30 (1996) 55-59.

"Label-free highly sensitive detection of (small) molecules by wavelength interrogation of integrated optical chips"; K. Cottier, M. Wiki, G. Voirin, H. Gao, R. E. Kunz; Science Direct; Sensors and Actuators B91 (2003) 241-251.

* cited by examiner

Figure 15
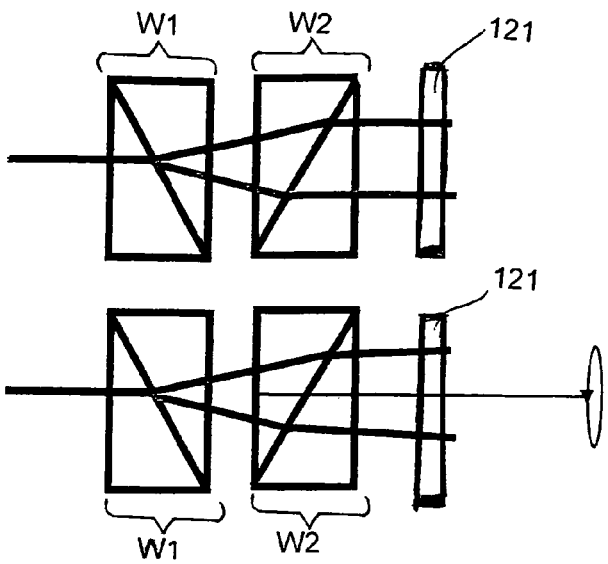
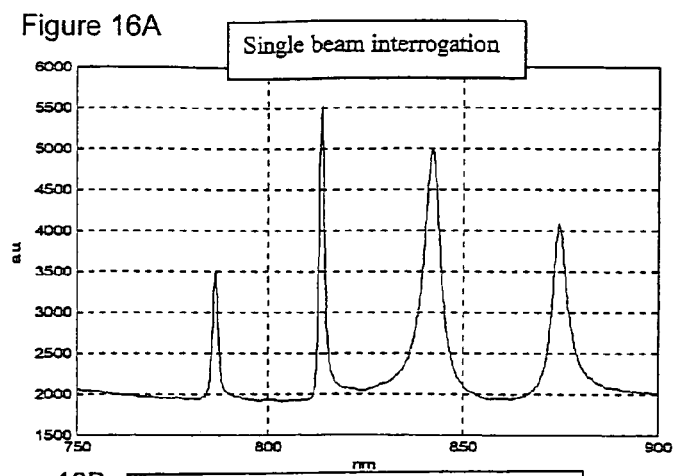
Figure 16A
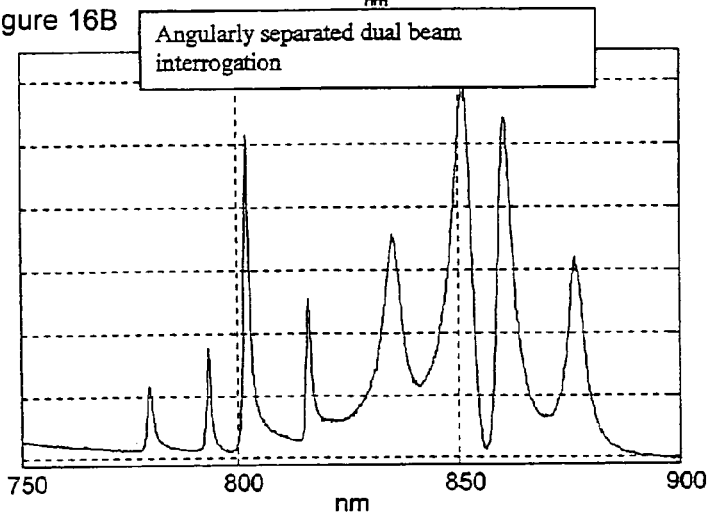
Figure 16B

OPTICAL INTERROGATION SYSTEMS WITH REDUCED PARASITIC REFLECTIONS AND A METHOD FOR FILTERING PARASITIC REFLECTIONS

FIELD OF INVENTION

The present invention pertains in general to optical interrogation systems that utilize optical sensors for label-independent detection of biological and chemical agents. More particularly, the invention relates to 1) a method for filtering parasitic reflections generated in a sensor that reflects polarized optical beam, and 2) an optical interrogation system capable of filtering parasitic reflections.

BACKGROUND

Optical interrogation systems that utilize evanescent field-based sensors are fast becoming a technology of choice for accurate label-free detection of a biological, biochemical, or chemical substance (e.g., cells, spores, biological or drug molecules, or chemical compounds). This technology typically involves the use of grating-coupled waveguides (GCWs) to sense a concentration change, surface adsorption, reaction, or the mere presence of a biological or chemical substance at the waveguide surface. Evanescent field-based sensors typically utilize a planar grating-coupled waveguide in direct contact with the compounds that are immobilized on the surface of the waveguide. When a biological, bio-chemical or chemical reaction happens at the surface of the waveguide, it changes the refractive index over a thin layer (few nanometers thick) and, as a consequence, the effective refractive index of the grating-coupled waveguide also changes. When a light beam is sent to the grating-coupled waveguide, the light couples into the GCW (under resonant condition) and then reflects at one specific angle and at one specific wavelength. (These angles and wavelengths are referred to as resonant angles and resonant wavelengths.) These angles and wavelengths are a function of the waveguide's effective refractive index.

More specifically, the resonant condition occurs only for a specific wavelength and angle of the incoming light beam, and changes in either angle or wavelength of reflected (resonant) light correspond to changes in the effective refractive index of the GCW. Thus, the optical interrogation system is used to sense a change in the effective index of the GCW, which enables one to determine whether or not a substance of interest is located within the sensing region of the GCW. Therefore, by measuring the resonant angles and/or the wavelengths of the reflected light, one can detect variation in the waveguide's effective refractive index and, thereby, detect the presence of biological, biochemical, or chemical substances.

In order for this technology to be viable, one must be able to accurately monitor the resonant angle(s) and/or the resonant wavelength(s). Optical interrogation systems utilizing evanescent field-based sensors employ two different interrogation methods. The first method is called the wavelength interrogation approach. It utilizes a collimated wide spectral band light beam incident at one at one specific angle at the GCW and uses a spectrometer to measure the (resonant) wavelength of the reflected light beam. The second method is called the angular interrogation approach. This method utilizes a single wavelength light beam, at multiple incidence angles to interrogate GCW. When utilizing this approach, the detector measures the (resonant) angle of the reflected light beam. The optical interrogation system that utilizes the angular interrogation approach is disclosed, for example, in U.S. Pat. No. 6,218,194 and is incorporated by reference herein.

However, in addition to reflecting light at the resonance wavelength or the resonance angle, grating-coupled waveguides (GCWs) also reflect light at other wavelengths and angles (parasitic geometric reflections), thus reducing the quality of the detected resonant signal. More specifically, because of these parasitic reflections one may see a low contrast weak resonance signal superimposed to a background of reflected light happening at all angles or wavelengths. The background lowers signal to noise ratio and makes the angular or wavelength measurement of the resonance less accurate. A second problem is caused by the reflections from the first (front) surface of the substrate or microplate, which are referred to herein as parasitic Fresnel reflections. Parasitic Fresnel reflections interfere with the resonance measurements and generate fringes in the angular or spectral space making the resonance detection very noisy and, due to temperature fluctuations and other factors, instable over time.

One example of wavelength interrogation system is shown on FIG. 1. A lens 108 collimates the light beam provided by the input fiber 106 which is connected to a broad spectral range light source 100. The collimated beam is then directed, at a specific angle, toward the sensor that includes the microplate 102 and the GCW 104. The reflected (resonant) light beam is collected by the lens 108 and imaged over the output fiber 107 which is connected to a spectrometer 101.

FIG. 2 shows an example of an angular interrogation system were the input fiber 106 is connected to a monochromatic light source 110 and the light beam is focused on GCW 104. After the light beams couples in GCW it is reflected at angles corresponding to the resonance condition and is imaged over a position sensitive detector 111.

However, as stated above, both of these approaches suffer from parasitic reflections which obscure the true resonance signal. To illustrate the problem, the curve 130 of FIG. 3 shows the simulated spectral resonance shape of the light reflected by the sensor. This curve is highly non symmetric and has a relatively bad contrast definition that is due only to the geometric reflections of the GCW across different wavelengths.

The problem of the parasitic Fresnel reflections happening at the first face of the microplate is illustrated by the curve 132 of FIG. 4. This resonance curve 132 is modulated at high frequency because of interference effects between the resonant light and the parasitic Fresnel reflections of the first face of the microplate 102. The phase and the frequency of this modulation is a function of the thickness of the microplate 102.

Some solutions for avoiding parasitic reflections, such as increasing the spatial and/or angular separation of the incident and reflected beams, are proposed in the literature (e.g., Cottier, K., et al., "Label-free Highly Sensitive Detection of (Small) Molecules by Wavelength Interrogation of Integrated Optical Chips," Sensors and Actuators B: Chemical, June 2003). The principle of this approach lies in defining the reader optics in such a way that the light is injected into one area of the grating-coupled waveguide and is collected from another area of the grating-coupled waveguide. Such a configuration is illustrated on FIG. 5. Hence, the detector is not collecting the parasitic reflections that occur at the input side of GCW, but rather collects only the light that has propagated into the grating coupled waveguide.

The solution described by Cottier, K., et al., however, is limited to unidirectional light propagation. It is important, in some cases, to collect the light that is propagating within the GCW in both directions. Therefore, Cottier's solution is not compatible with a double resonance approach, such as the one described, for example, in U.S. patent application Ser. No. 10/676,352, filed Sep. 30, 2003, by Gollier et al, which is incorporated by reference herein. Another limitation of the Cottier's technique is that it can only be utilized when the light propagation distances within the waveguide are larger than the input light beam diameter. Furthermore, in some cases, we want to measure different propagation modes (TE and TM). These modes have significantly different propagation distances. It is impossible, in utilizing the Cottier approach, to find a distance between the incident input beam (on GCW) and the collected output beam (from GCW) that allows us to keep all the modes and to simultaneously filter out parasitic reflections. Finally, in some other cases, it may be desirable to sending the light beam at normal incidence with respect to the GCW. However, in this case, a stationary wave is excited within the GCW. Thus, using the spatial separation suggested by the Cottier is not possible, because the light is not propagating within the GCW.

To illustrate those problems, the FIG. 6a shows a 4 resonances spectrum produced by the device of FIG. 1. The two peaks 140 on the left side of the spectrum curve represent the two TM modes propagating in opposite directions. The two peaks 141 on the right side of the spectrum curve represent the two TE modes propagating in the two directions. FIG. 6a illustrates that peaks 140 are difficult to detect due to parasitic reflections and that all peaks suffer from high frequency modulation. When the input and output light beams are separated as taught by Cottier, so as to filter out parasitic reflections around one of the resonant wavelengths corresponding to one of TM modes, the resonant wavelength corresponding to the second TM mode can no longer be detected. Furthermore, the two TE modes (which have smaller propagation distances within the waveguide) begin to disappear into the background noise (due to parasitic reflections) and are now difficult to detect. This is illustrated in FIG. 6b. Thus, Cottier method can not be utilized if one needs to detect both TM and TE (resonant modes), and/or if one needs to detect resonant modes propagating in opposing directions.

SUMMARY OF THE INVENTION

According to one aspect of the present invention the optical interrogation system comprises an optical sensor and an optical isolator that filters parasitic reflections introduced by the optical sensor.

According to one embodiment of the present invention a method for filtering parasitic reflections in a GCW based optical interrogation system comprises the steps of:
  a) providing an optical detection system including a light source;
  b) providing a sensor with at least one grating-coupled waveguide capable of reflecting a polarized light beam provided by the optical detection system;
  c) introducing the polarized light beam into the grating-coupled waveguide; and
  d) placing an optical isolator into an optical path within the optical detection system to filter: (i) Fresnel reflections generated from a first surface of the sensor, and/or (ii) geometric reflections of the grating-coupled waveguide.

According to one embodiment of the present invention the label-independent optical interrogation system for detecting biological, bio-chemical or chemical substances includes: 1) a sensor including a GCW with a surface having a sensing region capable of immobilizing biological, bio-chemical or chemical substances; 2) an optical detection system for monitoring the sensing region, said optical detection system comprising a light source, an optical delivery system, and a detection instrument,
  wherein the optical interrogation apparatus further includes an optical isolator to filter parasitic reflections generated by the sensor. According to some embodiments, the optical isolator may include a polarizer and either (i) a waveplate or (ii) Faraday rotator.

One of the advantages of the optical interrogation system of the present invention is its increased sensitivity for detection of biological, bio-chemical and chemical substances and decrease in background noise generated from parasitic reflections.

Another advantage of some of the embodiment of the present invention is that the optical isolator can separate an incoming light beam into a plurality of light beams in order to either sense different areas of one grating, or to sense spatially separated grating-coupled waveguides, thus enabling utilization of self referenced sensor approach.

Yet another advantage of the present invention is that both direction of light propagation and/or both TM and TE modes can be utilized to derive resonant signals from the sensor.

Additional features and advantageous of the present invention will be revealed in the following detailed description. Both the foregoing summary and the following detailed description and examples are merely representative of the invention, and are intended to provide an overview for understanding the invention as claimed. Reference to the accompanying figures and the following detailed description may convey a better understanding of the present invention.

BRIEF DESCRIPTION OF THE FIGURES

FIG. 15 illustrates schematically another exemplary optical isolator utilized in an optical interrogation system of the present invention. This optical isolator separates an incoming light beam into two light beams via two pairs of Wollaston birefringent prisms.

FIGS. 16a and 16b illustrate experimental results obtained in the configuration of FIG. 15.

DETAILED DESCRIPTION OF THE INVENTION

An optical interrogation system that includes a label-independent sensor functions by measuring either the angle or wavelength of a light beam that is introduced into a waveguide through a grating structure. Such a waveguide may be, for example, a planar waveguide that incorporates an optical grating. One method of optical interrogation involves fixing the incidence angle of the broad spectrum input beam and measuring the wavelength that gives the resonance (wavelength interrogation approach). Another approach involves using a monochromatic light source and measuring the angle that gives the resonance (angular interrogation approach).

As discussed above, prior art configurations suffer from "parasitic reflections" which obscure the true resonance signal. These parasitic reflections are introduced by the optical sensor and come from reflections on the first surface of the microplate/substrate or are generated by the geometric reflections of the GCW's surfaces. As a consequence of the presence of parasitic reflections, measurement accuracy is a degraded because of two possible effects: (i) parasitic reflections give a relatively bad signal to background ratio; and (ii) parasitic reflection can generate high frequency fringes (in either wavelength or angular space) if those reflections come from the first face of the microplate/substrate.

Figure 7:
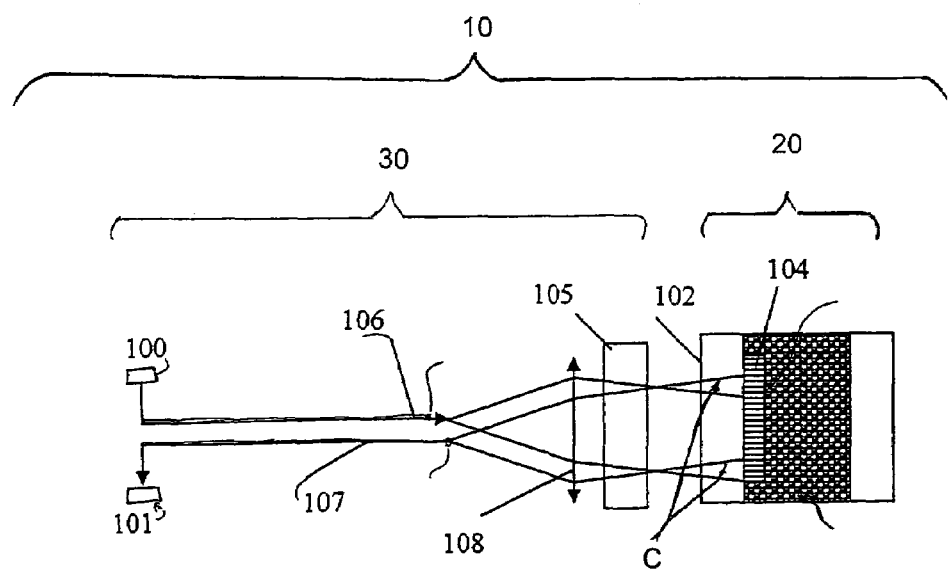
FIG. 7 illustrates schematically a GCW based optical interrogation system according to the first embodiment of the present invention. This optical interrogation system utilizes wavelength interrogation.

Reference will now be made in detail to the present preferred embodiments of the invention, examples of which are illustrated in the accompanying drawings. Whenever possible, the same reference numerals will be used throughout the drawings to refer to the same or like parts. One embodiment of the optical interrogation system of the present invention is shown in FIG. 7, and is designated generally throughout by the reference numeral 10.

In accordance with an embodiment of the present invention, the method for filtering parasitic reflections in a grating-coupled waveguide (GWC) based optical interrogation system includes the steps of: a) providing an optical sensor 20 with at least one grating-coupled waveguide that reflects a polarized light beam; b) providing an optical detection system 30 interacting with the sensor 20; c) introducing the light beam into the grating-coupled waveguide; and d) introducing an optical isolator into an optical path within the optical detection system to filter: (i) Fresnel reflections generated from a first surface of the optical sensor 20, and/or (ii) geometric reflections of the grating-coupled waveguide.

According to one embodiment, the optical interrogation system for detecting biological, bio-chemical or chemical agents comprises: 1) a sensor 20 including a GCW with a surface having a bio- or chemo-responsive layer; 2) an optical detection system 30 for monitoring the bio- or chemo-responsive layer, the optical detection system 30 including a light source, an optical delivery system, and a detection instrument, wherein the optical detection system also includes an optical isolator comprising a polarizer and either (i) a waveplate or (ii) Faraday rotator, to filter parasitic reflections generated by the optical sensor.

The optical isolator may comprise, for example, a polarizer and either a quarter wave plate or a Faraday rotator. The polarizer may also comprise a plurality of Wallaston prisms. Other optical isolators may also be utilized to filter parasitic reflections generated by the optical sensor 20.

EXAMPLES

The invention will be further clarified by the following examples.

Example 1

One example of optical (wavelength) interrogation system is shown on FIG. 7. The optical interrogation system 10 of FIG. 7 includes an optical sensor 20 and an optical detection system 30. The optical sensor 20 may include an air-fluid delivery system, comprising either macro or microfluidic passages designed to deliver biological or chemical analytes to the sensing region. The optical sensor 20 may have an optical-field sensing region and may comprise a substrate and a bio- or chemo-responsive layer. For example, the substrate can be modified with one or more coatings or layers of materials with desired surface chemistry, which enhance stable immobilization of said bio- or chemo-responsive layer. In this example, the optical sensor 20 of the wavelength interrogation system 10 includes a microplate or substrate 102 and at least one GCW 104 situated on the microplate or the substrate 102.

The optical detection system 30 includes a light source 100 suitable for provision of an input light beam, a spectrometer 101 for receiving and analyzing an output light beam, an optical isolator 105 located between the optical sensor 20 and the spectrometer 101, as well as input fiber 106, output fiber 107 and lens 108.

Figure 8:
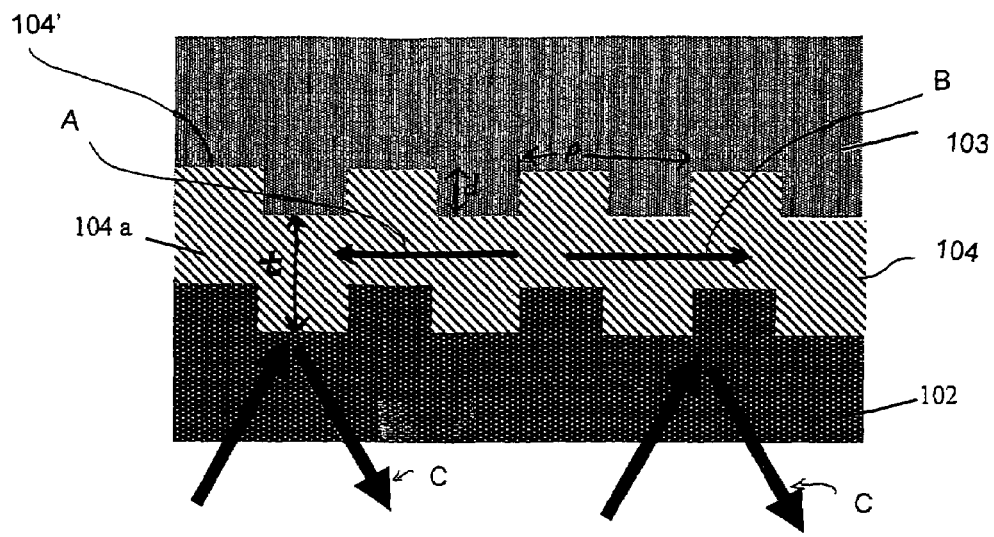
FIG. 8 illustrates schematically a GCW utilized in the optical interrogation system of FIG. 7.

In this embodiment the light source 100 provides broad spectral range (white) light that is coupled into the optical fiber 106. The light than exits from the output end 106a of the input fiber 106 and is collected by the lens 108. The lens 108 collimates the input beam leaving from the input fiber 106. The collimated beam is then directed toward the microplate or the substrate 102 of the optical sensor 20. The collimated beam impacts the microplate 102 and the GCW 104 at a predetermined angle. Some of the light is coupled into the waveguide/grating structure of the GCW 104. A schematic illustration of GCW 104 of this embodiment is shown in FIG. 8. The GCW 104 includes an optical waveguide 104a and a grating structure sandwiched between the substrate 102 and optically transparent fluid 103, and allows incoming light to propagate in two different directions in either TM and/or TE modes. It does not support light propagating in any other modes. The coupled light (TM and/or TE mode) propagates some distance within the GCW 104 (in one or two opposing directions as indicated by opposing arrows A & B) and reflects back (off the waveguide grating structure) towards the collimating lens 108. This reflected light carries information about the equivalent index of refraction which, in turn, provides information on whether or not biological, bio-chemical or chemical material is present on the surface of the GWC.

The reflected beam C is collected by the lens 108 and provided to the output fiber 107, which is connected to the spectrometer 101. The spectrometer 101 measures the wavelength(s) of the reflected light beam. The wavelength(s) of the reflected light beam is a function of the propagation mode of the light within the waveguide and the effective index of the grating coupled waveguide (GCW) 104. The effective index of the grating coupled waveguide is a function of the thickness of the GCW 104, refractive index $n_1$ of substrate 102, the refractive index $n_2$ of the waveguide, the refractive index $n_3$ of the fluid 103 (e.g., water), situated on top of the waveguide, as well as the refractive index $n_4$ of material(s) the presence of which we are trying to detect. More specifically, without the presence of this material(s), the detected reflected wavelength(s) (referred to as reference wavelength(s) herein) will have one set of values, which will be different than the wavelength(s) of the reflected light when either a biological, biochemical or chemical substance is present on the surface of the waveguide. Thus, the change in detected beam wavelength(s), from that of the reference wavelength(s), signifies the presence of biological, bio-chemical or chemical substance.

Figure 9:
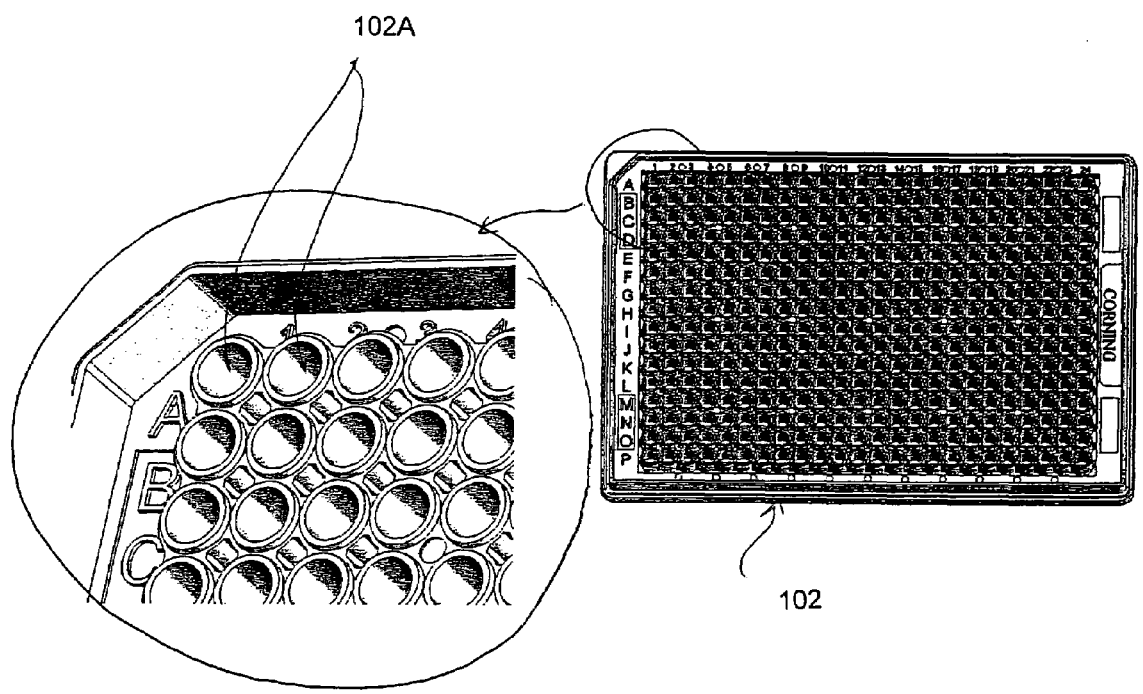
FIG. 9 illustrates microplate with a plurality of wells, each of the wells containing at least one GCW sensor.

In this example $n_1=1.5$; $n_2=2.1$; and $n_3=1.3$. These refractive indices are constant. The refractive index $n_4$ is not constant, and will depend on the specific material that is bound to the surface 104' of GCW 104. The grating coupled waveguide has a thickness t of about 190 nm, its depth d is about 50 nm and its pitch P is about 500 nm. Of course one may also use materials with other refractive indices and grating couple waveguides with other dimensions. In this embodiment both the TM mode and the TE mode propagates through the waveguide in two directions. Thus, the spectrometer 101 detects two wavelengths corresponding to the TM mode (one for each direction of propagation) and two wavelengths corresponding to the TE mode. The measurement is performed in the following fashion: First, GCW 104 is immersed in any non-reactive optically transparent fluid 103 (for example, de-ionized water) with a known refractive index $n_1$. A reference measurement is taken to determine the reference wavelength(s) of the light reflected from the GCW 104. Then, biological, bio-chemical, or chemical material is provided to the GCW through the fluid and some of this material binds to GCW. Since the fluid may now contain some of this material, which may effect the refractive index of the fluid, the fluid is then replaced with the new, uncontaminated fluid with the same index of refraction $n_1$ (e.g., new de-ionized water). The measurement is taken again and any difference in the wavelengths corresponds to the presence of the material on the GCW surface. A microplate may contain a plurality of GCWs, which may be interrogated simultaneously by multiple beams, which allow the user to simultaneously check for presence of a plurality of materials. FIG. 9 illustrates schematically a microplate 102 containing a plurality of wells 102A, each containing a GCW 104. The wells 102A may contain an optically transparent fluid 103, such as water, which covers the GCWs 104. A typical microplate may have, for example, 100 to 500 wells 102A.

Most of the remaining light propagates through the substrate and the GCW and is not reflected back towards the collimating lens 108. However, as discussed above, there are parasitic reflections generated by the incoming beam facing surface of the microplate/substrate and by the GCW.

In this embodiment, the optical interrogating system 10 of FIG. 7 also includes an optical isolator 105 situated between the collimating lens 108 and the microplate or the substrate 102. The optical isolator 105 eliminates parasitic reflections from the GCW 104, but allows the signal (i.e. information carrying) light C to propagate towards the lens 108, which focuses it at the input face 107' of the output fiber 107. The output fiber 107 delivers this light to the spectrometer 101.

Optical isolator 105 filters all reflected light (from the optical sensor 104) with the polarization which was not modified by the sensor 104. However, the reflected light with the modified polarization state will be going to be partly through the isolator 105. The polarization state of the parasitic reflections happening on the first face of the microplate 102 and the parasitic geometrical reflections of the CWG is not modified. Thus, both types of parasitic reflections are filtered by the optical isolator 105. On the other hand, the polarization state of the resonance is linear with a TE or TM orientation depending on the excited mode.

Example 2

Figure 10:
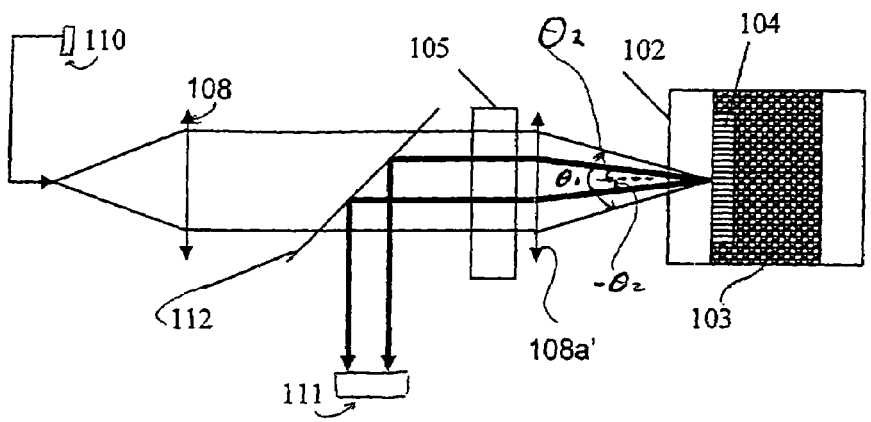
FIG. 10 illustrates schematically a second embodiment of the GCW based optical interrogation system of the present invention. This optical interrogation system utilizes angular interrogation approach.

FIG. 10 illustrates schematically an example of the optical interrogation system of the present invention that utilizes angular interrogation. This optical interrogation system utilizes a monochromatic light source 110. The input fiber is connected to the monochromatic source 110 and provides a diverging light beam to the collimating lens 108. The collimating lens 108 sends the collimated light beam towards an optical element 112, which passes it through the optical isolator 105. The light beam is then focused by the focusing lens 108a onto the grating of the GCW 104 with a large angular convergence angle $\theta_1$. The convergence angle of the focused beam is a function of the clear aperture of the lens 108a and its focal length. The optical isolator 105 minimizes or eliminates parasitic reflections from the substrate/microplate 102 and the GCW 104.

The light beam is reflected at two symmetric angles $\theta_2$ corresponding to the resonance condition, is collimated by the lens 108, passes trough the optical isolator 105 and is provided, vial optical element 112 to the detector 111. The detector 111 can be either a CCD camera, or any kind of Position Sensitive Detector.

Optical Isolator

Example 1

The above described embodiments of the present invention (shown in FIGS. 7 and 10) utilize an optical isolator 105. The optical isolator 105 filters parasitic reflections without requiring any spatial or angular separation between the input beam (incident on the GCW) and the collected output beam (reflected by the GCW). More specifically, FIGS. 7 and 10 show one exemplary implementation of the isolator 105 into a wavelength sensing optical interrogation system (FIG. 7), or into the optical interrogation system that utilizes an angular interrogation (FIG. 8). In these two embodiments of the optical interrogation systems the optical isolator 105 is a polarization sensitive isolator.

Figure 11:
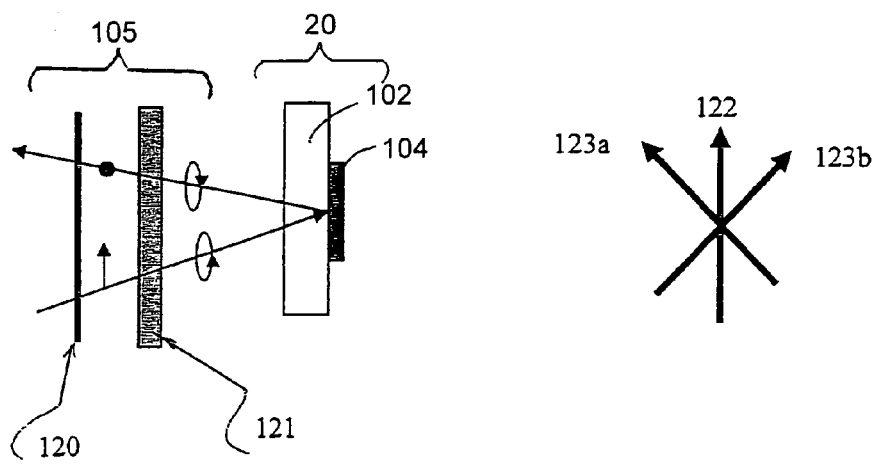
FIG. 11 illustrates schematically an optical isolator that includes a polarizer and a quarter waveplate.

An example of the polarization sensitive isolator 105 is shown schematically in FIG. 11. According to this embodiment, this isolator includes a linear polarizer 120 and quarter waveplate 121. The linear polarizer 120 has its polarization axis 122 oriented at 45 degrees relative to the polarization axis 123a and 123b of the quarter waveplate 121. The incoming light beam directed towards the GCW 104 passes through the linear polarizer 120 and becomes linearly polarized. The linearly polarized light then passes trough the quarter waveplate 121 and becomes circularly polarized. All parasitic reflections retain their original polarization and thus this light beam remains circularly polarized after reflection from GCW 104. The reflected circularly polarized light (parasitic reflections) passes through the waveplate 121 again, and undergoes polarization change. Its polarization axis changes to linear and is oriented at about 90 degrees with respect to the axis 122 of the polarizer 120. Thus, the polarizer 120 blocks parasitic reflections.

In the case of a resonance (i.e., the information carrying light beam that is coupled into and out of the waveguide), after reflection from GCW 104 the light beam polarization changes from circular to linear, the orientation of the polarization vector being dependent on the orientation of the GCW and on the light propagation mode (TE or TM). Assuming, for instance, that the light's polarization vector is along the one of the axis 123a or 123b of the quarter waveplate 121, the quarter waveplate 121 does not affect the polarization state of the propagating light and the polarizer will then transmit half of the optical power. The transmitted light (without parasitic reflections) will be provided to the detector to allow high accuracy detection and analysis.

Example 2

Figure 12:
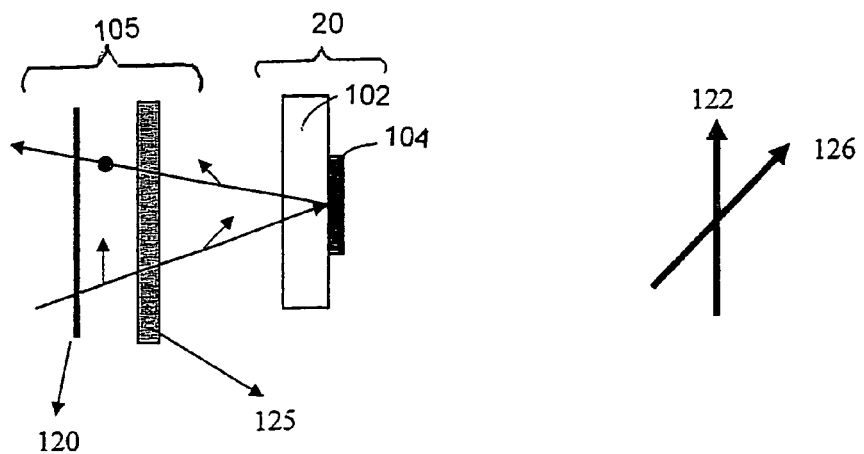
FIG. 12 illustrates schematically an optical isolator that includes a polarizer and a Faraday rotator.

Another example of the isolator 105 is shown schematically in FIG. 12. The isolator 105 of this example includes a polarizer 120 and a Faraday rotator 125. As the incoming light beam (propagating toward the GCW) passes through the polarizer 120 it becomes linearly polarized. After the light beam passes trough the Faraday rotator 125 its polarization is still linear, but the polarization vector 126 of the propagating light is rotated by 45 degrees. After the reflection, the polarization orientation (polarization vector) for the light associated with all parasitic reflections is not changed until this light propagates again trough the Faraday rotator, which again rotates the light's polarization axis by 45 degrees. Since the polarization axis of this light is now rotated by 90 degrees with respect to the axis 122 of the polarizer 120, parasitic reflections are filtered by the polarizer 120.

If the grating of the GCW 104 is oriented either along or perpendicular to the direction of the polarizer's polarization axis 122, the reflected light that corresponds to the resonance condition (i.e., the information carrying light beam that is coupled into and out of the waveguide and reflected back) will be linearly polarized with its polarization vector at 45 degrees with respect to the polarizer's axis 122. Thus this light beam will then be partly transmitted through the polarizer 120 and will be provided to the detector to allow high accuracy detection and analysis.

Figure 1:
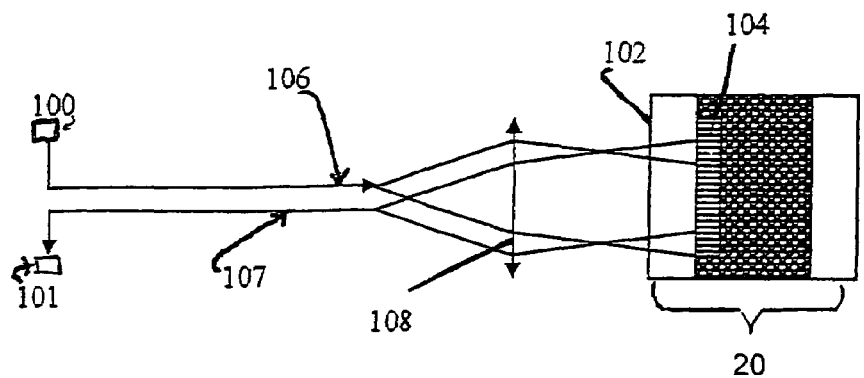
FIG. 1 illustrates schematically a prior art GCW (grated coupled waveguide) based optical interrogation system that utilizes wavelength interrogation.
Figure 2:
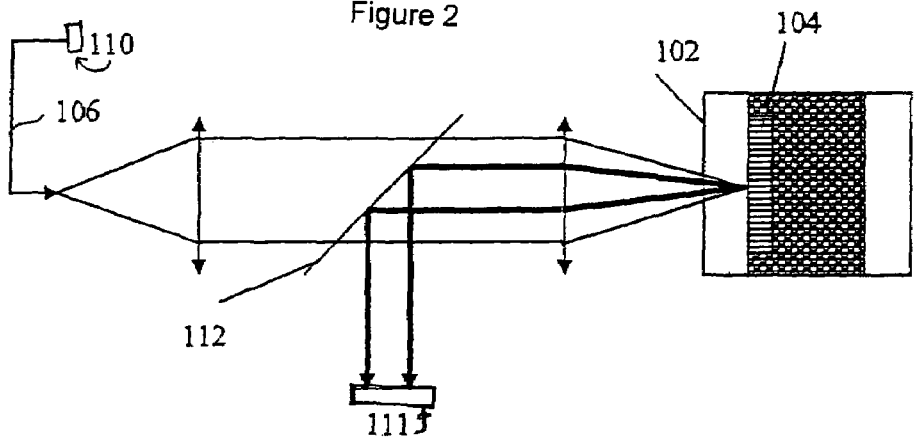
FIG. 2 illustrates schematically a prior art GCW based optical interrogation system that utilizes angular interrogation.
Figure 3:
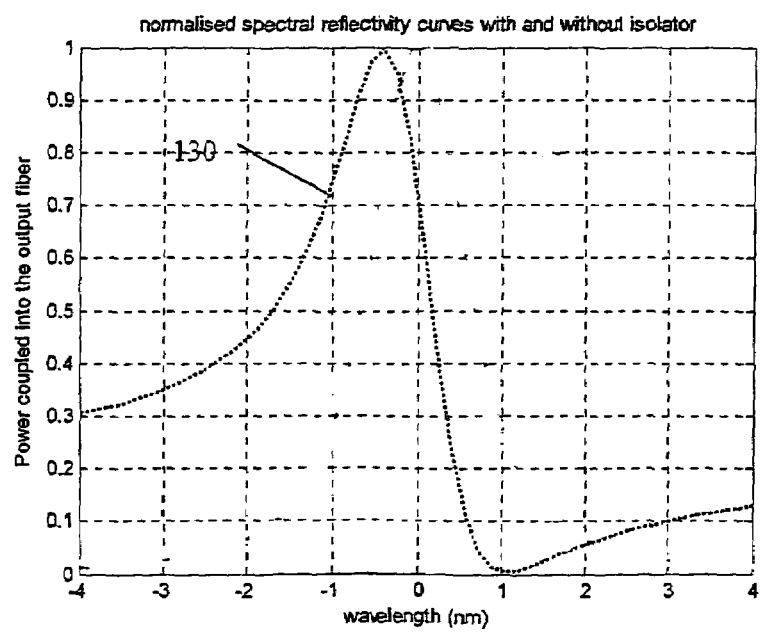
FIG. 3 illustrates wavelength resonance shape simulation of the optical interrogation system of FIG. 1.
Figure 4:
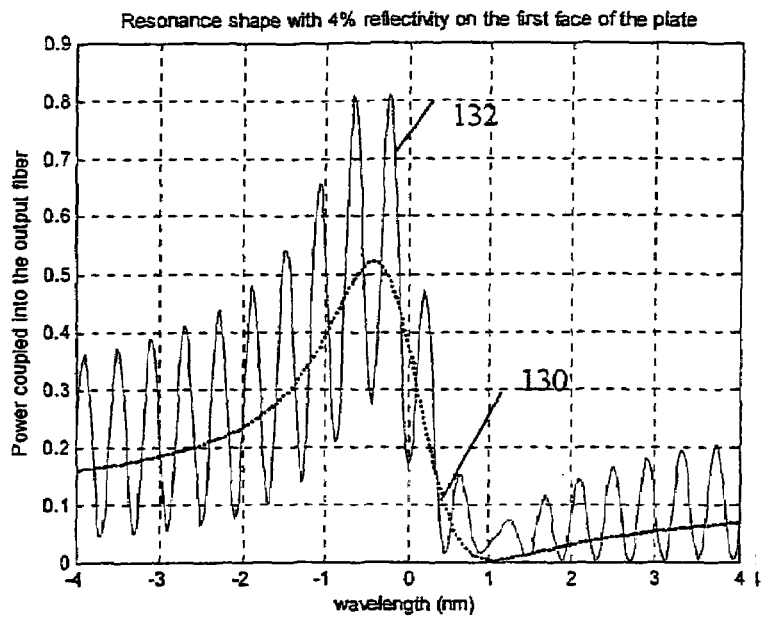
FIG. 4 illustrates the effect of the reflections from the first face of the microplate of the sensor utilized in the optical interrogation system of FIG. 1.
Figure 5:
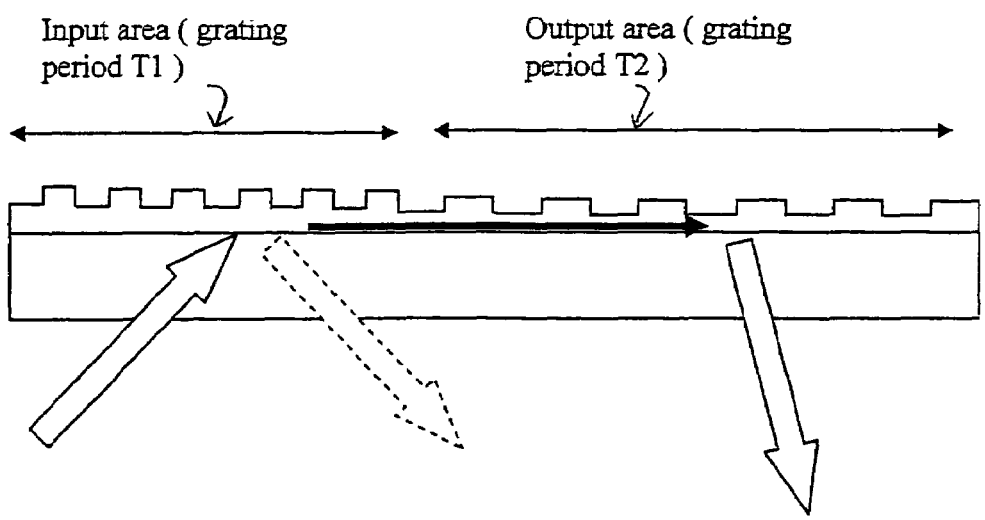
FIG. 5 illustrates schematically how parasitic reflections are reduced by spatially separating the input light beam and the light beam reflected by a GCW.
Figure 6A:
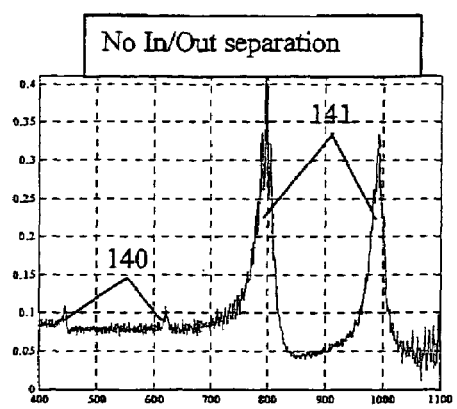
FIG. 6a provides experimental data measured by the optical interrogation system of FIG. 1. The data shows resonant wavelengths superimposed upon the background of parasitic reflections.
Figure 6B:
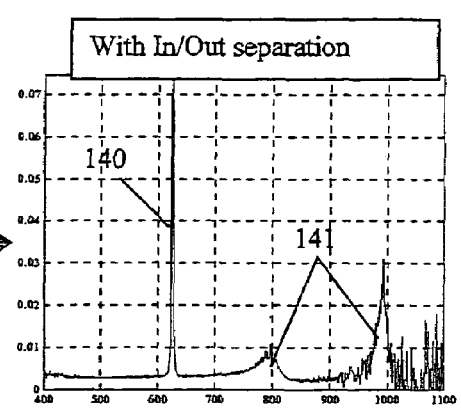
FIG. 6b is the curve of the resonant wavelengths data, with the parasitic reflections filtered according to a special separation method illustrated by FIG. 5.
Figure 13:
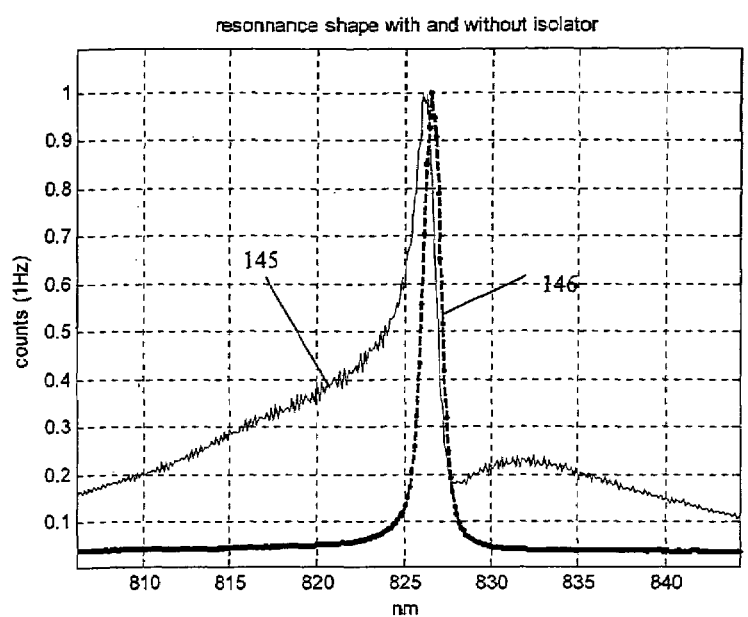
FIG. 13 depicts two experimental curves corresponding to two sets of resonant wavelengths measurements.

FIG. 13 depicts two resonance curves 145 and 146. Curve 145 corresponds to the resonance wavelengths that we measured in a wavelength interrogation system which does not utilize the optical isolator 105. Curve 146 corresponds to the resonance wavelengths that we measured with the wavelength interrogation system of FIG. 7, which includes the optical isolator 105. As we can see, the non filtered resonance (curve 145) presents a large asymmetry corresponding to the simulation of FIG. 3 and the contrast is relatively poor. Another problem that is visible on the curve 145 is the high frequency modulation that is generated by the reflection over the first face of the microplate. (The fact that this modulation does not present the large contrast shown on the simulation of the FIG. 4 is due to the fact that this modulation is partially filtered by the limited spectral resolution of the spectrometer. However, this modulation is large enough to significantly change the shape of the resonance and affect the repeatability of the measurements.) Curve 146 is a narrow, high contrast symmetric curve with no high frequency modulation. Thus, as described above, optical isolator 105 removes parasitic reflections from the returning beam and improves the quality of the optical interrogation system. Similar results can be also obtained by use of the optical isolator in the optical interrogation system that utilizes angular interrogation approach.

Example 3

Figure 14:
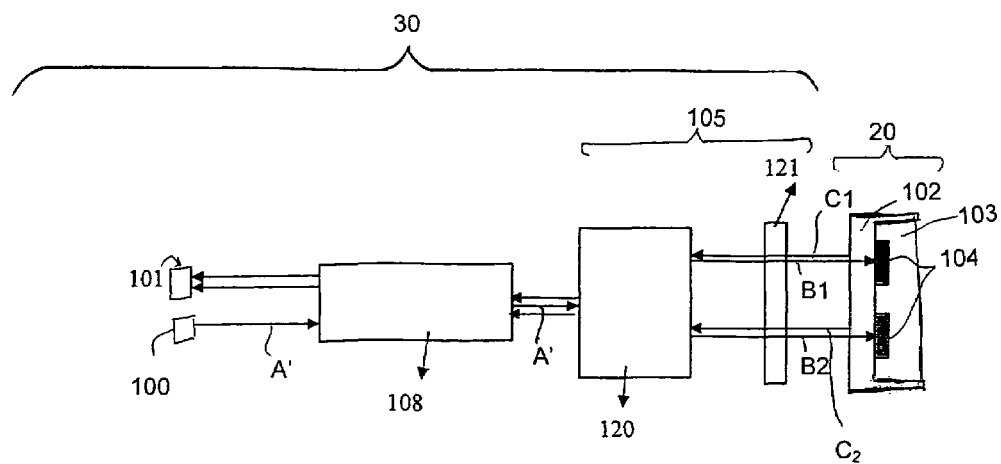
FIG. 14 illustrates schematically an optical isolator utilized in a GCW based optical interrogation system of the present invention. This optical isolator includes a birefringent beam displacement polarizer and generates two light beams for optical interrogation of GCWs.

This exemplary optical isolator (FIG. 14) is similar to the optical isolator of Example 1. However, the polarizer 120 of the isolator 105 is made of a birefringent beam displacing polarizing material, for example, YVO4, quartz or any other material presenting a large birefringence $\Delta n$, to separate the incoming beam into two differently (linearly) polarized input beam components. Having two input light beams instead of one light beams allows us to simultaneously interrogate at least two GCWs 104. This is illustrated schematically in FIG. 14. FIG. 14 shows that the non polarized beam input A' is separated, by the polarizer 120, into two beams $B_1$ and $B_2$. The input light beams $B_1$ and $B_2$ have linear polarizations that are perpendicular to one another, which become circularly polarized after crossing the waveplate 121. The two GCWs 104 have slightly different effective refractive indices (for example, due to slightly different thicknesses), so that they couple in and then reflect light $C_1$, $C_2$ characterized by slightly different resonance wavelengths. Thus, (after the two light beams were reflected by the GCWs and then re-combined by again passing through the polarizer 120) the reflected light can be simultaneously interrogated for presence of two different materials.

The two beams $C_1$, $C_2$ are combined by the polarizer 120 and the combined beams are presented to the output fiber and then to a spectrometer 101. The spectrometer then detects different resonance wavelengths corresponding to the two different GCWs 104. Thus, if the grating pitch or the effective index of the two GCWs 104 are different, the two reflected beams will be characterized by two sets of different wavelengths.

As described above, all parasitic reflections retain their original (incident) polarization (e.g. circular). The two reflected (parasitic) beams pass the waveplate 121 on their return from GCWs 104. The wave plate 121 changes polarization of each of the two returning beams by rotating them by 90 degrees. Thus, the polarization shift generated by the polarizer 120 is going in the opposite direction than it initially did. The parasitic reflections are then filtered out. Therefore, if both TM and TE modes that were propagating in two opposing directions within the two GCWs 104, the spectrometer 101 will measure a total of 8 wavelengths, Note that the FIG. 12 represents a case were the GCWs 104 are interrogated at normal incidence and the optical isolator 105 includes the waveplate 121. It can be shown that this approach is also compatible with non normal incidences and with using a Faraday rotator 125, instead of the quarter wave plate 121.

The approach illustrated in FIG. 14 allows us to interrogate at least two different GCWs. A similar approach, but utilized with two identical GCWs, may also be used to detect any environmental change while detecting the presence of the biological, bio-chemical or chemical substance. That is, splitting an input light beam into two beams allows each of the light beams to interrogate a different GCW. One of the GCWs provides reference measurements (by monitoring sensor drift over time and/or environmental changes, for example, temperature variations, or the angular changes in the incident beam), while the other GCW is used to detect the presence of the biological, bio-chemical or chemical substance. This interrogation system is referred to as self referenced system. An environmental change would change the pitch of the grating and the effective index of the reference GCW, causing resonant wavelength(s) or the resonant angle to shift to a slightly different wavelength(s) or angle. The other, identical GCW registers changes that are due to all changes—i.e., changes due to biological, bio-chemical or chemical substances as well as changes due to environmental changes, angular changes, etc. Thus, the two GCWs provide two different measurements and the difference between the two sets of data corresponds only to the presence of the detected substance and is not due to environmental changes. However, because wavelengths corresponding to both resonances are imaged over the same output fiber, the wavelengths corresponding to the two GCWs need to be spectrally separated to be able to differentiate between them. This can be done, for example by utilizing polarization sensitive angular separation of the two returning differently polarized beams.

Example 4

This optical isolator according to another embodiment of the present invention is illustrated in FIG. 15. This embodiment utilizes two Wallaston prisms $W_1$, $W_2$ and a quarter waveplate 122 situated between the second Wallaston prism $W_2$ and the sensor 20. By inserting a first Wollaston prism $W_1$ into the light beam, we obtain two diverging light beams that have orthogonal polarizations that propagate into different directions. When the two light beams pass through the identical second Wollaston prism $W_2$, the two propagating light beams become parallel again and are spatially separated, as shown in FIG. 15. The beam separation is a function of the angle of the prisms and of the distance between them. If one of the two prisms $W_1$, $W_2$ is rotated around its optical axis, it is possible to change the orientation of one light beam with respect to the other light beam. The resonance wavelength being a function of the incidence angle, the effect of the rotation of one prism will be to shift the spectrum of one optical path with respect to the other optical path. So, even if the reference grating and the measurement grating are identical, a rotation of the prism allows to shift the spectra each other so that it is possible to dissociate the resonances from the reference and from the measurement channels.

The FIGS. 16a and 16b show the experimental results obtained with the configuration of the FIG. 15. Without angular misalignment, we obtain four resonances that correspond to the two TE and TM modes (FIG. 16a). When introducing an angular misalignment, the peaks are split and we end up with 8 dissociated resonance peaks. (FIG. 16b)

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

I claim:

1. A label-independent optical interrogation system for detecting biological, bio-chemical or chemical agents, the detection system comprising: 1) an optical sensor including a GCW with a surface having a sensing region capable of immobilizing biological, bio-chemical or chemical substances; 2) an optical detection system for monitoring said sensing region, said optical detection system comprising a light source, an optical delivery system, and a detection instrument, wherein said optical interrogation apparatus further includes an optical isolator filtering and substantially eliminating parasitic reflections generated by said optical sensor.

2. The label-independent optical interrogation system according to claim 1, wherein said optical isolator comprises a polarizer and either (i) a waveplate or (ii) faraday rotator.

3. The label-independent optical interrogation system according to claim 1, wherein said optical isolator comprises at least one pair of Wallaston prisms.

4. The label-independent optical interrogation system according to claim 1, wherein said optical isolator separates said light beam to create two light beams.

5. The label-independent optical interrogation system according to claim 4 wherein said two light beams are collimated light beams.

6. A method for filtering parasitic reflections in a GCW based optical interrogation system, the method comprising:
   a) providing an optical detection system including a light source;
   b) providing a sensor with at least one grating-coupled waveguide capable of reflecting a polarized light beam provided by said optical detection system;
   c) introducing the polarized light beam into said grating-coupled waveguide; and
   d) placing an optical isolator into an optical path within said optical detection system to filter and substantially eliminate: (i) Fresnel reflections generated from a first surface of said sensor, and/or (ii) geometric reflections of said grating-coupled waveguide.

7. The method for filtering parasitic reflections according to claim 6, wherein said optical interrogation system measures resonant wavelengths of the light reflected by said sensor.

8. The method for filtering parasitic reflections according to claim 6, wherein said optical interrogation system measures resonant angles of the light reflected by said sensor.

9. The method for filtering parasitic reflections according to claim 6, further including the step of separating said light beam into two beams.

10. The method for filtering parasitic reflections according to claim 9 wherein said two light beams are collimated beams.

11. The method for filtering parasitic reflections according to claim 6, wherein said optical isolator includes at least one polarizer.

12. The method according to claim 11, wherein said polarizer separates said light beams to create two collimated beams.

13. The method according to claim 6, wherein said optical isolator:
   i. comprises a polarizer and either (i) a waveplate or (ii) faraday rotator; and
   ii. sends a non-linearly polarized light to said sensor.

* * * * *